United States Patent
Maget et al.

(10) Patent No.: US 9,550,008 B2
(45) Date of Patent: Jan. 24, 2017

(54) TWO-PART, SYRINGE-BASED ELECTROCHEMICAL DISPENSER

(75) Inventors: Henri Maget, San Diego, CA (US); Mark Johansson, San Diego, CA (US)

(73) Assignee: M&R Consulting Services, Inc., San Diego, CA (US)

( * ) Notice: Subject to any disclaimer, the term of this patent is extended or adjusted under 35 U.S.C. 154(b) by 396 days.

(21) Appl. No.: 13/271,982

(22) Filed: Oct. 12, 2011

(65) Prior Publication Data
US 2012/0091170 A1 Apr. 19, 2012

Related U.S. Application Data (60) Provisional application No. 61/392,873, filed on Oct. 13, 2010.

(51) Int. Cl.
| | | |
|---|---|---|
| *B67D 7/10* | (2010.01) | |
| *A61L 9/12* | (2006.01) | |
| *A01M 1/20* | (2006.01) | |
| *B67D 7/02* | (2010.01) | |
| *B67D 7/72* | (2010.01) | |

(52) U.S. Cl.
CPC .............. *A61L 9/12* (2013.01); *A01M 1/2044* (2013.01); *B67D 7/0244* (2013.01); *B67D 7/72* (2013.01); *Y10T 137/2931* (2015.04)

(58) Field of Classification Search
CPC ...... A01M 1/2044; B67D 7/72; B67D 7/0244; A61L 9/12
USPC ........................... 222/1, 325, 386.5, 389, 397
See application file for complete search history.

(56) References Cited

U.S. PATENT DOCUMENTS

| | | | | |
|---|---|---|---|---|
| 1,471,091 A | * | 10/1923 | Bessesen | 222/386.5 |
| 3,876,115 A | | 4/1975 | Venus et al. | 222/183 |
| 3,981,415 A | | 9/1976 | Fowler et al. | 222/95 |
| 4,113,151 A | * | 9/1978 | Brown et al. | 222/324 |
| 4,341,348 A | | 7/1982 | Dearling | 239/34 |
| 4,734,092 A | * | 3/1988 | Millerd | 604/67 |
| 4,776,499 A | | 10/1988 | Magid | 222/386.5 |
| 4,902,278 A | | 2/1990 | Maget | |
| 5,427,870 A | | 6/1995 | Joshi et al. | 429/27 |
| 5,445,462 A | | 8/1995 | Johnson et al. | 401/132 |
| 5,681,435 A | | 10/1997 | Joshi | |
| 5,785,688 A | | 7/1998 | Joshi | |
| 5,899,381 A | | 5/1999 | Gordon | |
| 5,928,194 A | | 7/1999 | Maget | |

(Continued)

OTHER PUBLICATIONS

U.S. Appl. No. 08/308,647, filed Dec. 18, 2008, Maget et al.

*Primary Examiner* — Patrick M Buechner
(74) *Attorney, Agent, or Firm* — Steins & Associates, P.C.

(57) ABSTRACT

A Two-part, Syringe-based Electrochemical Dispenser. The dispenser consists of a disposable syringe-like fluid storage reservoir and a reusable fluid driver. The driver is located at the proximal end of a conventional syringe; the fluid exit port at the distal end. The driver generates a gas that inflates an elongated bladder situated within the filled syringe. Expansion of the bladder releases liquid at a rate nearly identical to the gas generation rate. The dispenser is held in a vertical position with the distal end pointed downward. Liquid is released drop-wise onto a porous material from which it can evaporate. A battery-driven electrochemical oxygen generator is the gas source. Means to attach the dispenser in its vertical position are provided. Such dispensing devices can be used to release pheromones, repellants, insecticides, fragrances, etc.

8 Claims, 8 Drawing Sheets

(56) References Cited

U.S. PATENT DOCUMENTS

| | | | |
|---|---|---|---|
| 5,932,204 A | 8/1999 | Joshi | 424/76.1 |
| 5,938,640 A | 8/1999 | Maget et al. | 604/145 |
| 6,042,704 A | 3/2000 | Joshi et al. | |
| 2005/0023371 A1* | 2/2005 | Joshi et al. | 239/60 |
| 2008/0308647 A1* | 12/2008 | Maget et al. | 239/34 |

* cited by examiner

TWO-PART, SYRINGE-BASED ELECTROCHEMICAL DISPENSER

This application is filed within one year of, and claims priority to Provisional Application Ser. No. 61/392,873, filed Oct. 13, 2010.

BACKGROUND OF THE INVENTION

1. Field of the Invention

The invention herein relates to vapor release devices/dispensers. More particularly it relates to small two-part dispensers with disposable fluid reservoirs and re-usable fluid pumping mechanisms.

2. Description of Related Art

Commodity fragrance releasers and pheromone dispensers must be economical in order to be deemed commercially feasible by potential consumers. Three such devices are described in U.S. Pat. No. 5,928,194 for "Self-contained liquid microdispenser" (Maget I), U.S. Pat. No. 6,383,165 for "System for achieving a controlled low emission rate for small volumes of liquid solutions" (Maget V) and in U.S. Pat. No. 7,681,809 for "Electrochemical dispenser" (Maget VI).

Most prior art dispensers include an integral battery-powered gas generation unit, such as described in U.S. patent application Ser. No. 12/413,546 for "Electrochemical Gas Generator and Cell Assembly," as well as in Maget VI. The Ser. No. 12/413,546 device does not, however, embody a dispenser having two parts (one being replaceable).

One prior device does teach a two-part fluid dispenser—Maget VI, as well as the system taught by U.S. Pat. No. 5,938,640 for "Two-part fluid dispenser" (Maget II). The teachings of Maget V and Maget VI are incorporated herein by reference since devices are described therein that includes an elongated dispenser similar to the device described herein, but with the following important distinctions: (i) fluid release in the prior system is from the top of the elongated reservoir and not the bottom, and (ii) the pumping mechanism of Maget V is an integral part of the disposable releaser.

Another important difference and improvement over Maget VI is the re-usable feature of the driver. While the fluid reservoir will require regular replenishment, the gas generator will not. Since the gas generator has a long service life (several years), the driver can be expected to operate up until the exhaustion of the onboard battery capacity. Even then, replacing the onboard batteries will provide another gas generator operating cycle. Therefore the cost per use of the driver is amortized over the multiple uses of the driver (i.e. multiple battery replacements and fluid replenishments.)

Since the fluid reservoir of the instant design is based upon a plastic syringe, the cost of replacement of the disposable component is expected to be as low as that of plastic syringes, a commodity product, that are produced in billions of units/year by the health care industry.

While it may seem trivial, to place the syringe with the distal end pointing downward, the reader is assured that this is not the case. In fact, by employing this configuration, all of the fluid can be eventually evacuated from the syringe barrel, whereas in the device of Maget VI, some of the liquid would be entrapped at the base of the elongated reservoir. Furthermore, compression of the bladder of the Maget VI device requires ever-increasing forces (pressures) to expel the fluid or ever-decreasing delivery rates, since the bladder eventually needs to collapse completely in order to surrender the contents that can be trapped in the bladder folds. In contrast, in the present invention, the bladder expands outward, with its outer dimensions being confined by the rigid syringe wall. Gravity assists the syringe driver in forcing the liquid contents towards the distal end.

Similarly, replacing the fluid receiver of Maget V with a porous plastic cup of the present invention facilitates the attachment of the fluid emanation surface to the syringe. The combination of an airtight bladder and an airtight generator render it possible to hold the syringe "upside-down" without any loss of fluid. Additionally, fluid stream discontinuity between the Luer tip and the porous receiver prevents fluid "streaming" (capillary extraction of fluid from the syringe) as well as preventing the introduction of ambient air into the syringe. If either of these were permitted, it would be impossible to control the fluid delivery rate, and therefore the rate of emanation. Finally, the orientation of the dispenser allows for the solar cells to be mounted to the top of the gas generator and still be exposed to sunlight.

SUMMARY OF THE INVENTION

In light of the aforementioned problems associated with the prior devices and methods, it is an object of the present invention to provide a Two-part, Syringe-based Electrochemical Dispenser. The dispenser should be practical and low-cost, while being capable of releasing fluids into the environment under controlled conditions. The dispenser should allow the user to operate the device in a position such that all of the fluid is released. It is a further object that the fluid storage reservoir is a disposable (and economical) syringe-based unit. It is yet another object that the gas generator driver be reusable, and only require replacement of the battery power source. Still further, it is an object to provide users with means to set and later readjust the delivery rate of the dispensed fluid. It is still another object that the dispenser utilize energy from solar or artificial light sources to power the driver thereby reduce the periodicity of the battery replacement. Furthermore, if solar-powered, it is an object that alternate embodiments of the invention become inactive in absence of sunlight or on rainy days. It is a final object to provide users with a simple syringe-attachable porous plastic receiver that receives the fluid in droplet form for future evaporation.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, of which:

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide a Two-part, Syringe-based Electrochemical Dispenser.

Figure 1:
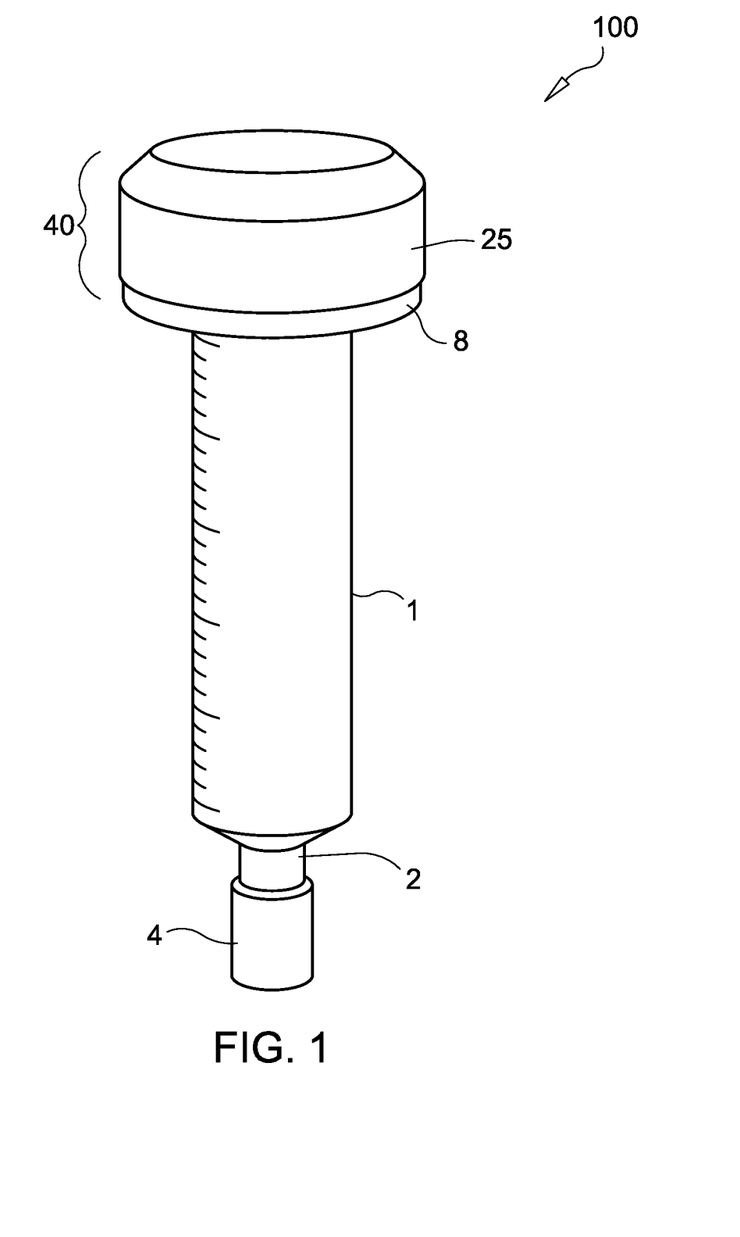
FIG. 1 is a perspective view of a preferred embodiment of the dispenser of the present invention.

The present invention can best be understood by initial consideration of FIG. 1. FIG. 1 is a perspective view of a preferred embodiment of the dispenser 100 of the present invention. The dispenser 100 employs a conventional syringe barrel 1, having a gas generator driver head assembly (generically 40 here) attached to replace the conventional syringe's plunger.

Figure 2:
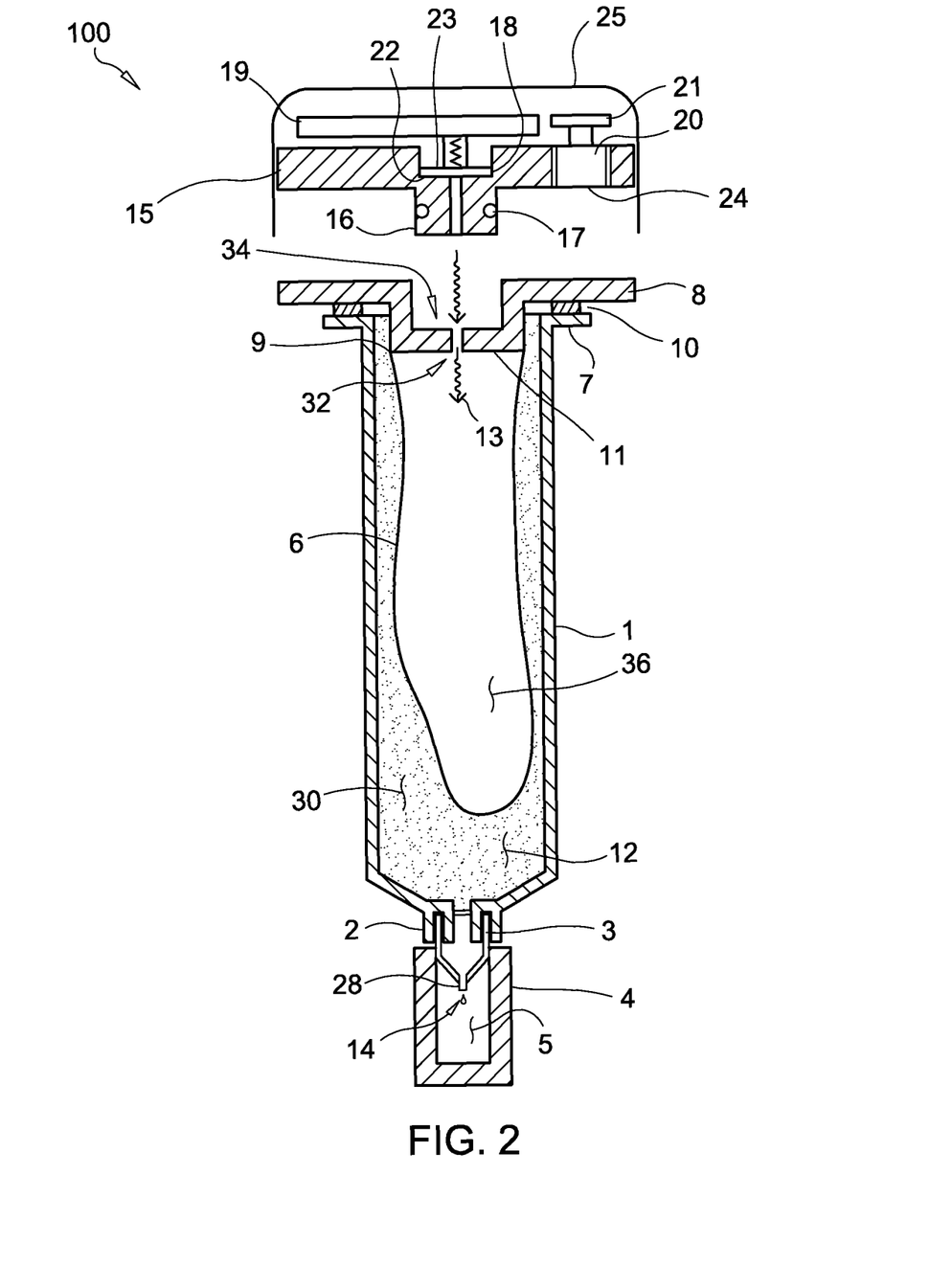
FIG. 2 is a cutaway side view of the dispenser of FIG. 1.

The driver head assembly 40 is housed within a protective cover 25 that can be removed for maintenance purposes (e.g. battery changeouts). The head assembly 40 has a liquid- and air-tight seal to the syringe head 8. The tip end of the syringe barrel 1 terminates in a conventional Luer lock 2, to which a dispense cup 4 is threadedly attached. FIG. 2 provides additional detail regarding this novel device.

FIG. 2 is a cutaway side view of the dispenser 100 of FIG. 1, illustrating the components and assembly of the dispenser refill and driver. The refill consists of a conventional plastic syringe barrel 1 terminated at its distal end by a female Luer lock 2. The syringe can be made from polyethylene, polypropylene, glass, etc. A syringe head 8 is bonded or welded using an air-tight seal 10 to the proximal face of the syringe flange 7. The plastic head flange 8 is made of polyethylene or other plastic that is generally compatible with the thin-film plastic bladder 6 material. The bladder 6 is heat-staked (thermally bonded) at attachment area 9 on the outer surface of the head flange boss 11, to form a leak-free connection between the two.

The thin-film bladder 6 is designed to fill the syringe barrel 1 internal volume when it is fully expanded. Prior to its use, the bladder 6 is compressed to occupy only a small fraction of the syringe chamber 30. In actuality, a nominal 50 mL syringe with an internal volume in excess of 60 mL, in absence of its plunger, will hold in excess of 50 mL of fluid, therefore the compressed bladder occupies less than 5-10 mL of the syringe volume. Bladder 6 material is selected for chemical compatibility with fluids 12 to be delivered and low permeation to oxygen 13 delivered to (and stored in) the bladder. Example materials include multi-layered films where one layer is compatible with the syringe head material, such as Saranex, with a film thickness generally between 25 and 125 microns.

The male Luer lock 3 at the distal end of the syringe barrel 1 holds a dispense nozzle 28 with an aperture allowing for the formation of small discrete droplets 14. The nozzle 28 delivers fluid to the evaporation chamber 5 formed within a porous-walled plastic cup 4. Once dispensed within the chamber 5, the droplets 14 will be allowed to evaporate and exit through the porous walls of the cup 4. Cups having the desired properties are known to be produced by POREX, Inc and/or Genpore, (among other sources). The level of porosity of the plastic cup 4 is defined (i.e. created) during manufacturing. The properties of the plastic material, (hydrophobic, hydrophilic, oleophobic, etc.) is selected depending upon the fluid to be delivered. It is expected that the porosity will generally be in the range of 20-200 microns.

An important operating requirement of this fluid releaser is that the fluid droplets 14 are not permitted to contact the porous plastic receiver walls (before they are released into the cup 4). If contact occurs, it may result in fluid droplets being withdrawn from the syringe through capillary action. This is undesirable, because in such an event the liquid fluid release rates would not be controlled by the gas generator current but by another withdrawing mechanism.

The syringe driver base 15 (and associated elements) is also depicted in FIG. 2. The diameter of the base 15 is generally of the same order of magnitude as the syringe head 8. A boss 16 extends from the bottom face of the base 15, and is cooperatively designed to mate with the well 34 formed in the head flange 8 using a ring seal 17. The ring seal 17 is provided to ensure a leak-free interface between syringe barrel 1 (at the head flange 8) and driver base 15. The upper part of the boss 16 has a cavity into which an electrochemical module (ECM) 18 will be bonded in an air-tight manner. ECM's of this type have been described by Maget et al in U.S. Pat. No. 6,010,317 (Maget IV—"Electrochemical cell module having an inner and an outer shell with a nested arrangement").

The ECM's cathode 23 is exposed to air, and its counter-electrode (the anode 22) releases oxygen according to the following reactions, already described in many of the prior Maget patents:

Cathode: $O_2 + 4H^+ + 4e^- \rightleftarrows 2H_2O$

Anode: $2H_2O \rightleftarrows O_2 + 4H^+ 4H^+ + e^-$

Overall process: $O_2(air) \rightleftarrows O_2(pure, compressed)$

More specifically, the use of an electrochemical oxygen generator to operate a glass syringe has been described by Maget et al in U.S. Pat. No. 5,971,722 (Maget III) for the delivery of 100 mL of fluid (drugs) over period of 1 to 7 days. However in that instance, since a syringe plunger is used, considerable force was required to prevent rubber plunger or plunger seal to "seize" on the internal syringe wall. This problem is avoided in the current invention since the bladder material is selected for its ability to deform (i.e. inflate) at low internal pressure differentials.

Components assembled on the surface of the driver base 15 are the power source 19 (alkaline batteries), an activation switch 20, and a circuit board 21 on which is a current controller. The components are connected electrically as depicted in FIGS. 5B, 6B and 7B. Once the switch 20 is activated by pressing button/activation arm 24, battery power is provided to the current controller, which maintains a constant current through the ECM 18 regardless of cell impedance. Since the current controller requires a minimum input voltage of 1.4 volts, the circuit requires two (2) series-connected batteries. Alternatively, a voltage booster circuit could operate the system from a single battery; however at a cost of system longevity since inefficiencies inherent in such booster circuits would result in increased battery energy demands. For example, AA batteries have an energy storage capacity for continuous operation at low currents, with voltage as far down as 0.9 volts, of about 2500 mAhr. Since the current consumption of the ECM 18 is 4.4 mAhr per cubic centimeter of oxygen generated, the two series-connected batteries can generate about 570 cc of oxygen gas.

Factoring in system inefficiencies, then, the rated volume of liquid delivered in such case would be approximately 400-500 mL. Consequently, the battery would yield approximately 8-10 deliveries of 50 mL syringes. In a scenario wherein a flow rate of 1 mL/day is produced, each pair of AA batteries could deliver fluid continuously for over 1 year. Similarly, 2AAA batteries could operate for one-half of one year, and C-size batteries for over 3 years. The elements of the device 100 are depicted again in FIG. 3.

Figure 3:
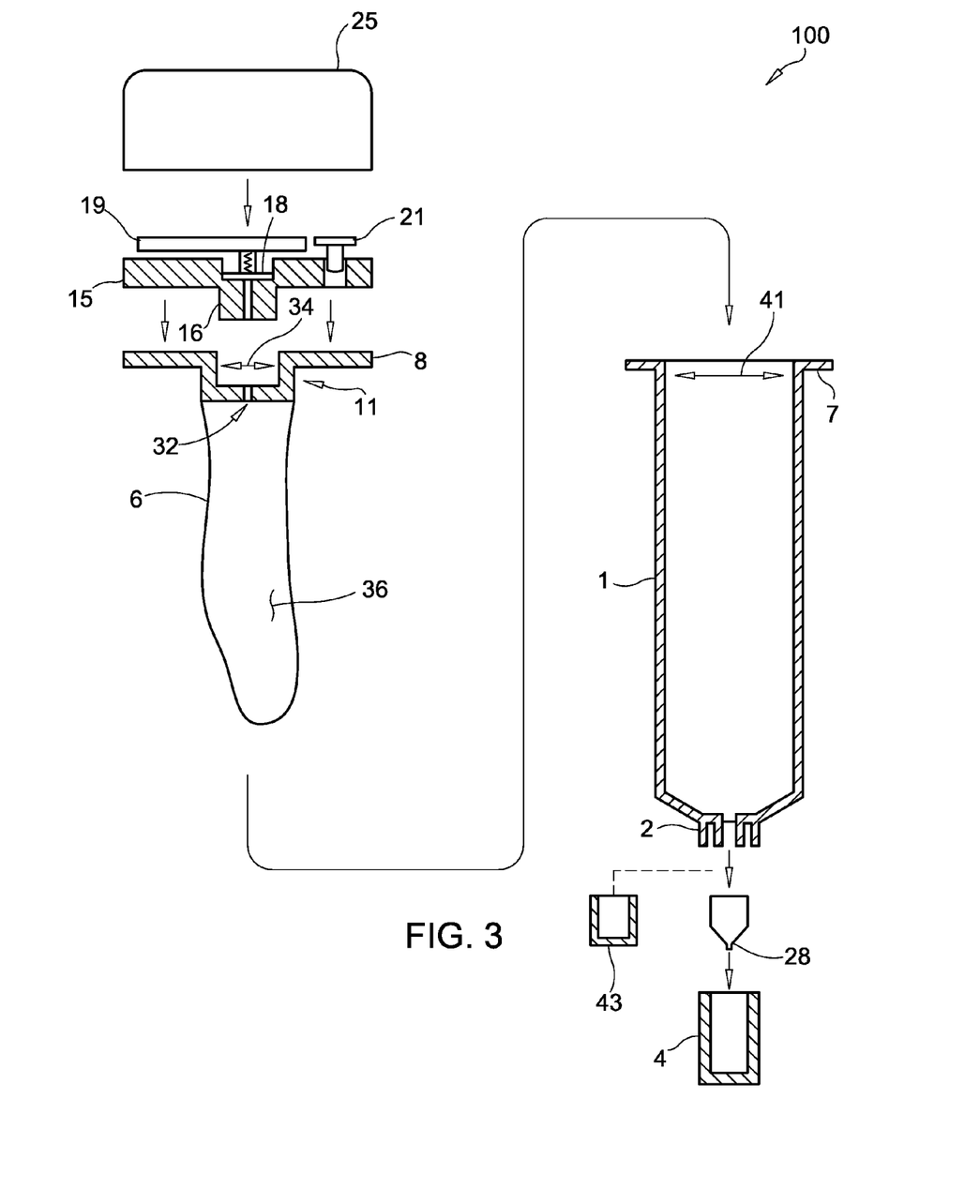
FIG. 3 is an exploded cutaway side view of the dispenser of FIGS. 1 and 2.

FIG. 3 is an exploded cutaway side view of the dispenser 100 of FIGS. 1 and 2. The syringe barrel 1 is essentially the same as employed by a conventional (disposable) syringe. Either a storage cap 43 or dispense nozzle 28 threadedly engages the luer lock 2 extending from the tip end of the syringe barrel 1. The storage cap 43 is utilized when the barrel 1 has been pre-filled with the dispense chemical (i.e. the syringe 1 has been filled, and the head flange 8 and bladder 6 have been attached/sealed to the syringe barrel 1). This unit may be referred to as a replacement cartridge. The replacement cartridge, then, consists of syringe 1, syringe head 8 attached to bladder 6, and (optionally), the storage cap 43.

Specifically, in order to rejuvenate an expended dispenser 100, a user need only obtain a replacement cartridge, attach the existing driver head assembly (see FIG. 1) to it, and then replace the storage cap 43 with a suitable dispense nozzle 28 and cup 4.

To fill the syringe place the cartridge "upside-down", i.e. with the syringe's Luer lock 3 in the upright position, and fill the syringe by using a blunt (to prevent damaging the bladder) needle inserted in Luer entry port. Once filled, the cartridge can be optionally fitted with a Luer cap (e.g. for transportation) or cup 4 (when in operation).

As discussed above in connection with FIG. 2, the thin film bladder 6 is bonded to the head flange 8 adjacent to the head flange boss 11, in order to provide a gas-tight seal thereto. The head flange boss 11 is configured to be insertible into the upper throat 41 of the syringe barrel 1. There is a airtight seal (element 10, see FIG. 2) between the upper surface of the syringe flange 7 and the bottom surface of the head flange 8. This seal prevents liquid from escaping, and also is the mechanism that retains the attachment between the head flange 8 and the syringe flange 7.

Figure 4A:
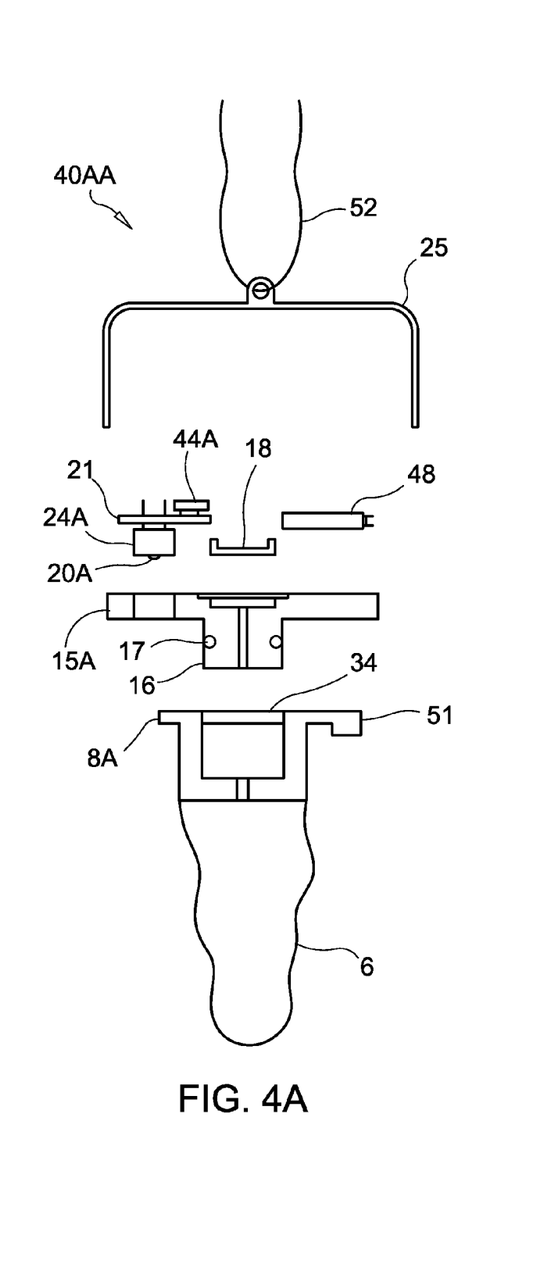
FIG. 4A is a partial cutaway side view of an alternate driver head assembly.
Figure 4B:
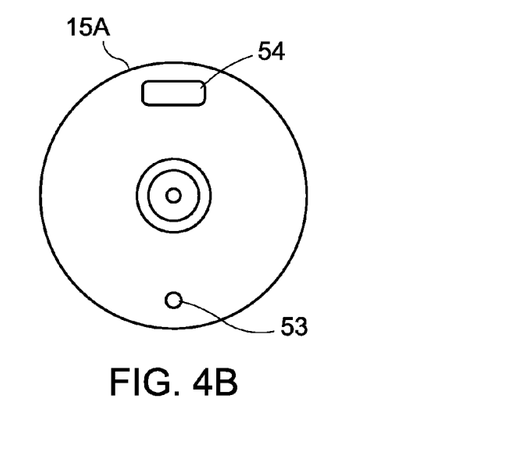
FIG. 4B is a top view of the driver base of the assembly of FIG. 4A
Figure 4C:
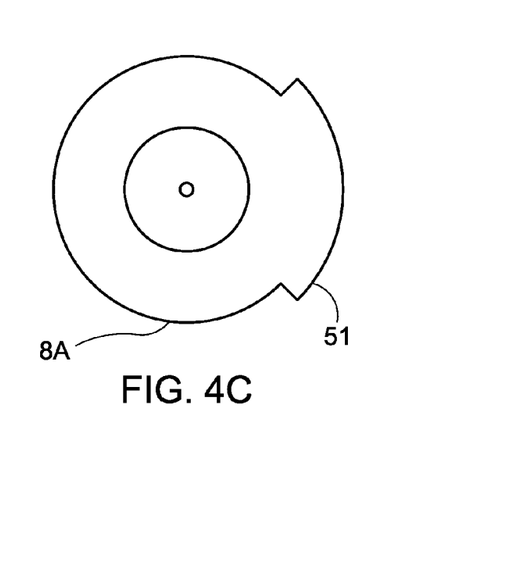
FIG. 4C is a top view of the head flange of FIG. 4A.

The driver base 15 is formed with a driver boss 16 extending therefrom. The boss 16 and head flange well 34 are cooperatively designed so that the boss 16 fits into the well 34. A ring seal (element 17, see FIG. 2) creates a gas-tight seal between these two elements so that all of the gas being generated by the module 18 is directed through the inflation orifice 32 and into the bladder chamber 36. The power source 19 (batteries, solar power and/or other power source) and the other elements in the driver head assembly are protected from the environmental elements by the protective cover 25 detachably attached to the driver base 15. FIGS. 4A-4C depict an alternate switching design.

FIGS. 4A, 4B and 4C are a partial cutaway side view of an alternate driver head assembly 40AA, a top view of the driver base 15A of the assembly 40AA, and a top view of the head flange 8A of the assembly 40AA, respectively. This alternate design 40AA comprises a switch aperture 54 formed in the driver base 15A, through which a snap-action pushbutton switch 24A protrudes downwardly. An example of a suitable switch 24A is provided by C&K Corporation (CKN10158-ND).

The switch 24A and button 20A protrude downwardly from the circuit board so that the button 20A will engage the extension segment 51 protruding from the head flange 8A. In order to activate or deactivate the ECM 18, one need only rotate the driver base 15A in relation to the head flange 8A. When the base 15A is rotated sufficiently (rotating about the driver boss 16), the pushbutton 20A will engage the extension segment 51 and thereby drive the pushbutton 20A upward to activate the switch 24A. Activation of the switch 24A will supply electrical power to the ECM 18. Continued rotation of the base 15A relative to the flange 8A (or reverse rotation) will eventually result in the pushbutton 20A being released over the edge of the extension segment 51, thereby deactivating the ECM 18. It should be understood that the radial protrusion of the extension segment 51 in the depicted design is only one option—other approaches may be used (e.g. an aperture or peg on the flange 8A, rather than a radially-extending protrusion).

Since both the driver base 15A and head flange 8A are deeply engaged into cap 25 and therefore not visible, in its preferred form, extension segment 51 is extended downward along syringe barrel 1 to make it visible to the user. A marking inscribed on cap 25 will allow user to identify the location that the extension segment 51 needs to be in (relative to the cap 25) for start-up (or deactivation).

The protective cap 25 fits tightly past driver head 15A, and onto and below the head flange 8A to prevent moisture or dust to reach the electronics circuitry. Since ECM 18 consumes oxygen (from air), to prevent the ECM from becoming oxygen-starved, a small, 1 mm diameter air intake port 53 is provided in driver base 15A. Cap 25 is provided with hanging wire 52 to facilitate its being hung from an external structure (e.g. a tree branch, etc.). Each version of the head assembly 40 (and 40A, 40AA, 40B and 40C) could be provided with the intake port 53 and hanging wire 52, as well. The following figures depict a variety of embodiments of the instant invention.

Figure 5A:
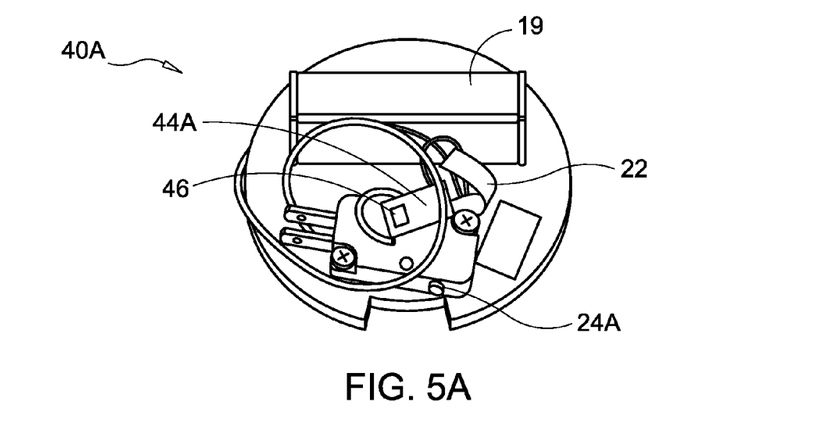
FIG. 5A is a perspective view of a single current driver head assembly of the present invention and FIG. 5B is a diagram of a preferred circuit for said assembly.
Figure 5B:
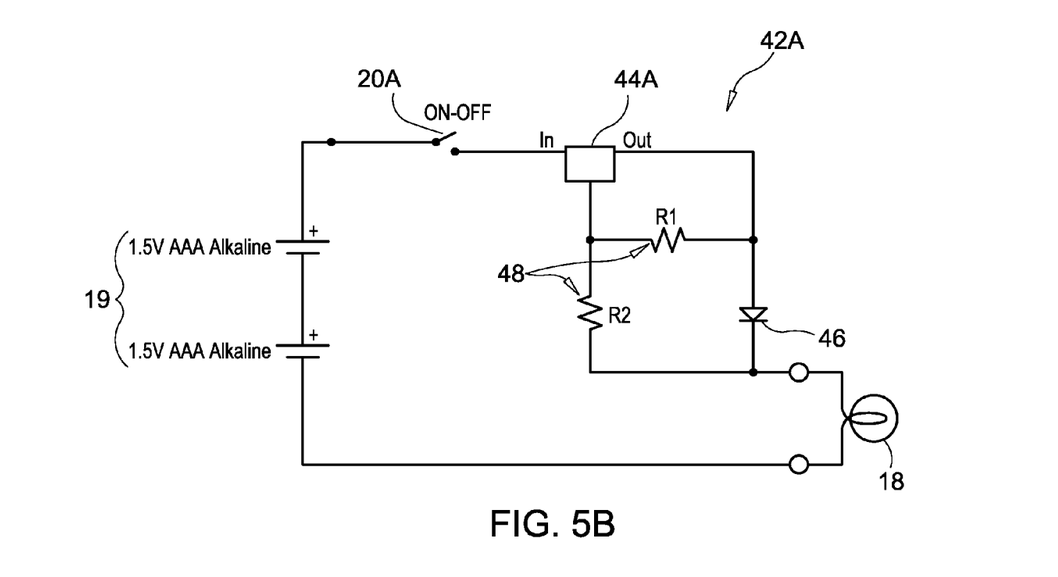

FIG. 5A is a perspective view of a single current driver head assembly 40A of the present invention (having its protective cover removed) and FIG. 5B is a diagram of a preferred circuit 42A for said assembly 40A. Various current controlling options can be implemented. The simplest system (not depicted here) involves a single resistor, which defines the current according the relationship:

$$(V_B - V_R)/R = I$$

where $V_B$ is the battery voltage, $V_C$ is the ECM voltage and

R is the resistance in the circuit.

For small currents (i.e. <1 mA), the battery voltage is stable over long time periods. If the ECM voltage is also quasi-stable, then the current can be pre-set by resistor selection. However, in the single current versions, the current is at the mercy of two voltages, one decreasing in time (battery supply voltage) the other increasing in time (ECM demand voltage).

For example, a system having: battery voltage $V_B$=1.50 volts; ECM voltage $V_C$=0.90 volts and R=3 kilo-ohms, results in a current of 0.2 mA equivalent to a gas generation rate of 1.1 cc/day that in turn yields a fluid pumping rate of about 1 mL/day. If $V_B$ decreases by 20 millivolts and $V_C$ increases by 20 mV, then the current decreases by 5% to 0.19 mA, and a pumping rate reduction of about 5 (five) percent.

If this variation is unacceptable, current controllers are preferred. The circuit and driver for a single flow rate device are FIGS. 5A and 5B. The single current driver 40A consists of 2 alkaline batteries 19, a current controller 44A (such as National Semiconductors LM334M or equivalent), a Fairchild Semiconductors diode (1N457A) 46 and 2 resistors 48 to set the current. The controller 44A output will drop off at a voltage below 1.4 volts, and therefore the need for 2 batteries 19. For a desired current of 200 micro-amps the resistor values are R1=681 and R2=6810 ohms. The start-up switch 20A holds a push button actuator 24A that is activated by means of an activation arm (not shown) mounted on the syringe head (not shown).

Figure 6A:
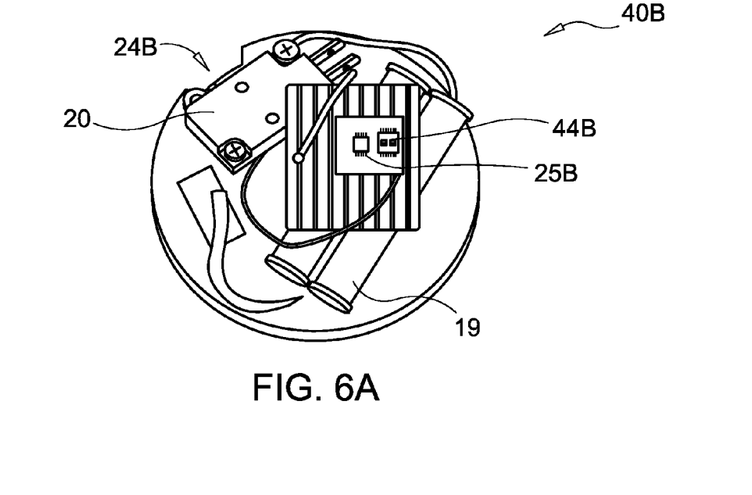
FIG. 6A is a perspective view of a multi-current driver head assembly of the present invention.
Figure 6B:
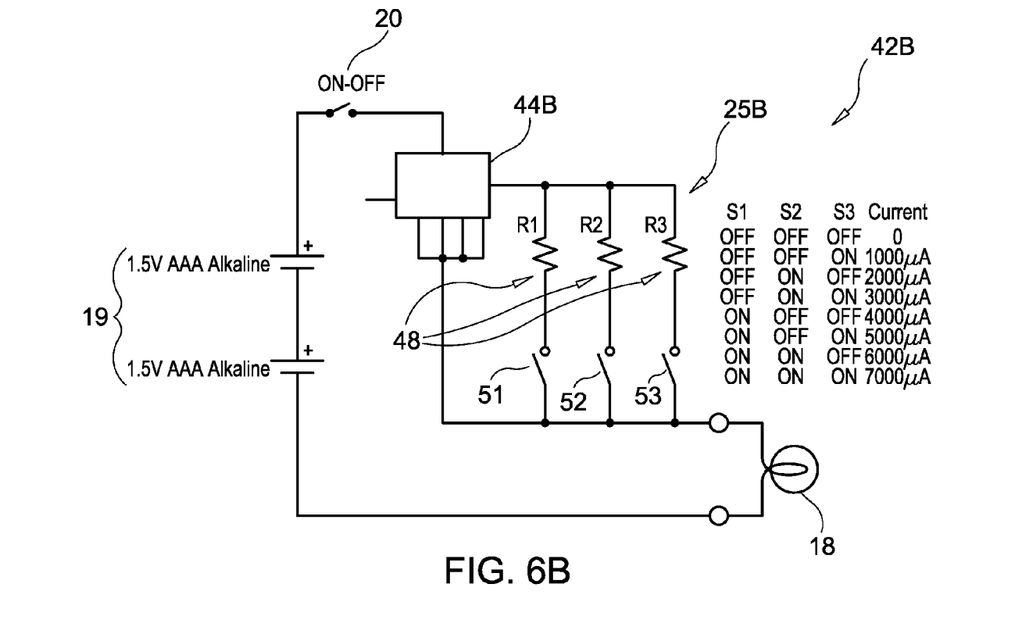
FIG. 6B is diagram of a preferred circuit for said assembly.

FIG. 6A is a perspective view of a multi-current driver head assembly 40B of the present invention, and FIG. 6B is diagram of a preferred circuit 42B for said assembly 40B. The multiple current driver 40B, 42B of FIGS. 6A and 6B is identical to the single current unit (see FIGS. 5A and 5B), except for a 3-position switch [e.g. C&K Components DIP switch (CKN3002-ND)] 25B and additional resistors. In FIG. 6A, the DIP switch 25B and current controller 44B are mounted on a surfboard circuit board with 3 resistors 48, namely R1=169, R2=340 and R3=681 ohms. As depicted in the embedded matrix, such an arrangement allows for selection of 8 different currents, varying in increments of 100 microamps and a range of from 0 to 0.7 mA. This equates to an oxygen generation rate range of from 0 to 3.86 cc/day in increments of 0.50 cc/day, or the equivalent of between about 0 and 3.5 mL/day of fluid delivered.

Figure 7A:
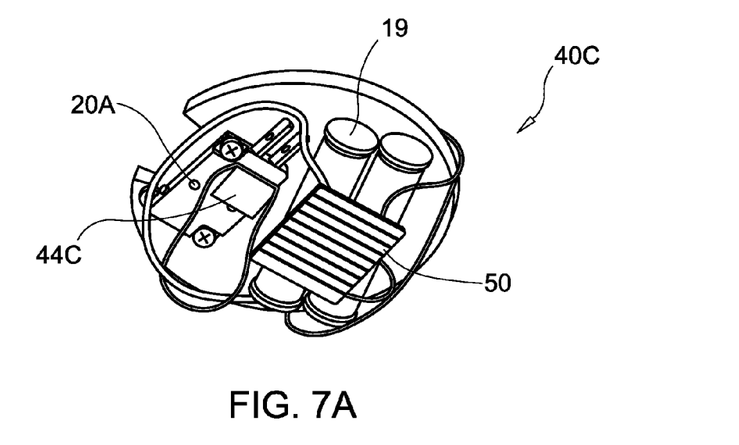
FIG. 7A is a perspective view of a single current driver head assembly of the present invention, including solar power.
Figure 7B:
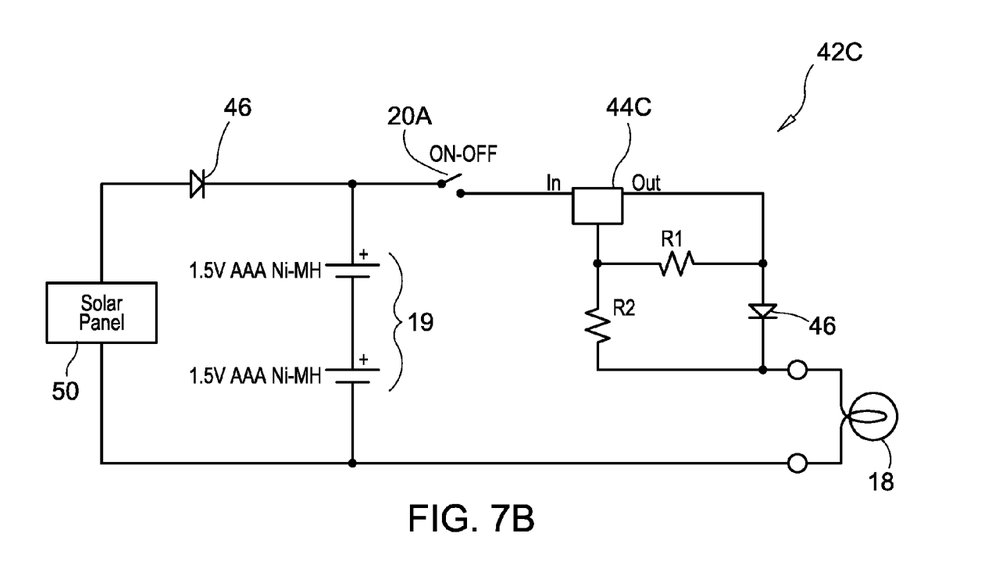
FIG. 7B is a diagram of a preferred circuit for said assembly.

FIG. 7A is a perspective view of a single current driver head assembly including solar power 40C of the present invention, and FIG. 7B is a diagram of a preferred circuit 42C for said assembly 40C. The depicted system 40C, 42C is configured to generate a single current of 200 microamps. In this configuration, the circuit includes 2 rechargeable AAA nickel-metal hydride batteries 19, a Solarbotics SCC2422 solar panel 50, diodes 1N5818 47 and 1N457A 46, resistors R1=681 ohms and R2=6810 ohms, and current controller LM334M 44C.

Rechargeable batteries are required for nighttime operation, but are charged while the solar panel 50 is exposed to sunlight. Either solar cells benefiting from direct or indirect solar illumination, or solar cells capable of operation from illumination with artificial light can be used. It is possible to eliminate the batteries 19 from the circuit, but doing so will only allow operation during periods where the panel 50 is illuminated. Such a system would release fluid only during daylight or presence of artificial light. This might be desirable, for example to avoid the release of expensive pheromones at night or in inclement weather (when the insects to be affected by the pheromones are not active). Alternatively, other techniques can be implemented such as the use of optical transducers that are light activated. Fluid release would be terminated as soon as the panel ceases to be illuminated.

Clearly, the advantages of having an independent, autonomous, active electrochemical process that can be turned on and off, has an adjustable chemical release rate, and that can be self-powering when exposed to sunlight, represent considerable improvements over the integrated systems of Maget IV.

It will also be obvious to others that more complex control functions can be incorporated in circuits that can bear higher costs, such as timers, interrupted delivery, pulsed delivery, etc.

Operating the Dispenser (in Reference to FIGS. 1-7, as Appropriate)

The syringe refill barrel 1, separated from the driver base 15, is first filled by way of female Luer lock 2 at the distal end of the syringe 1 (the porous receiver 4 and attached male Luer lock 3 having been previously removed). The bladder 6 is pre-shrunk by applying gas pressure to its exterior via Luer lock 2 or by applying a vacuum via port 32.

After filling the syringe 1 the Luer lock 2 is capped by means of a conventional Luer cap. The syringe and its fluid charge can now be transported (without the receiver cup 4 and nozzle 28 attached).

To ready the unit 100 for dispensing of the fluid, the user removes the conventional Luer cap and replaces it by a fluid receiver cup 4 (which is pre-bonded to nozzle 18). Next, the driver base 15 is inserted onto head flange 8, which will release a small fluid bolus. Once the two parts 15 and 8 are mated, the user rotates the driver base 15 into the designated OFF position (i.e. to place it in stand-by). To start the dispenser 100, the user simply rotates the driver base 15 onto the designated ON position (relative to the flange 8). In that position pressure is applied to the contact switch 24 by means of the activation arm 20, and the unit is started.

The single rate unit does not require any further action. Once in the ON position, the multiple-rate unit requires that the desired current be selected via the 3-way switch 25B located on the driver head assembly 40B under cover 25. The codes for the different switch positions determine specific rates. In other versions of the device 40B, other start-up mechanisms are possible.

During operation, the rate can be changed (or the releaser can be stopped), by operation of the switch 24B, or by rotating the driver into the OFF position. To replace or refill the syringe barrel 1, the user need only disengage and remove the barrel 1 and repeat the previous start-up procedures. In some instances the empty syringe 1 can be re-used, however, in that case the user is advised to pressurize the syringe chamber 30 in order to collapse the bladder before re-using it.

To replace the batteries, the user removes protective cover 25 to access the batteries 19. The protective cover 25 should be installed during operation, since it protects the driver head assembly 40 from environmental elements (rain, dust, etc.). The cover 25 fits over both driver and syringe heads (8 and 7, respectively) to prevent water from reaching the electronics and the activation arm 20. In the case of solar cell-powered drivers, solar panel 50 is embedded in a water-proof manner in cover 25.

Performance of the Dispenser

Figure 8:
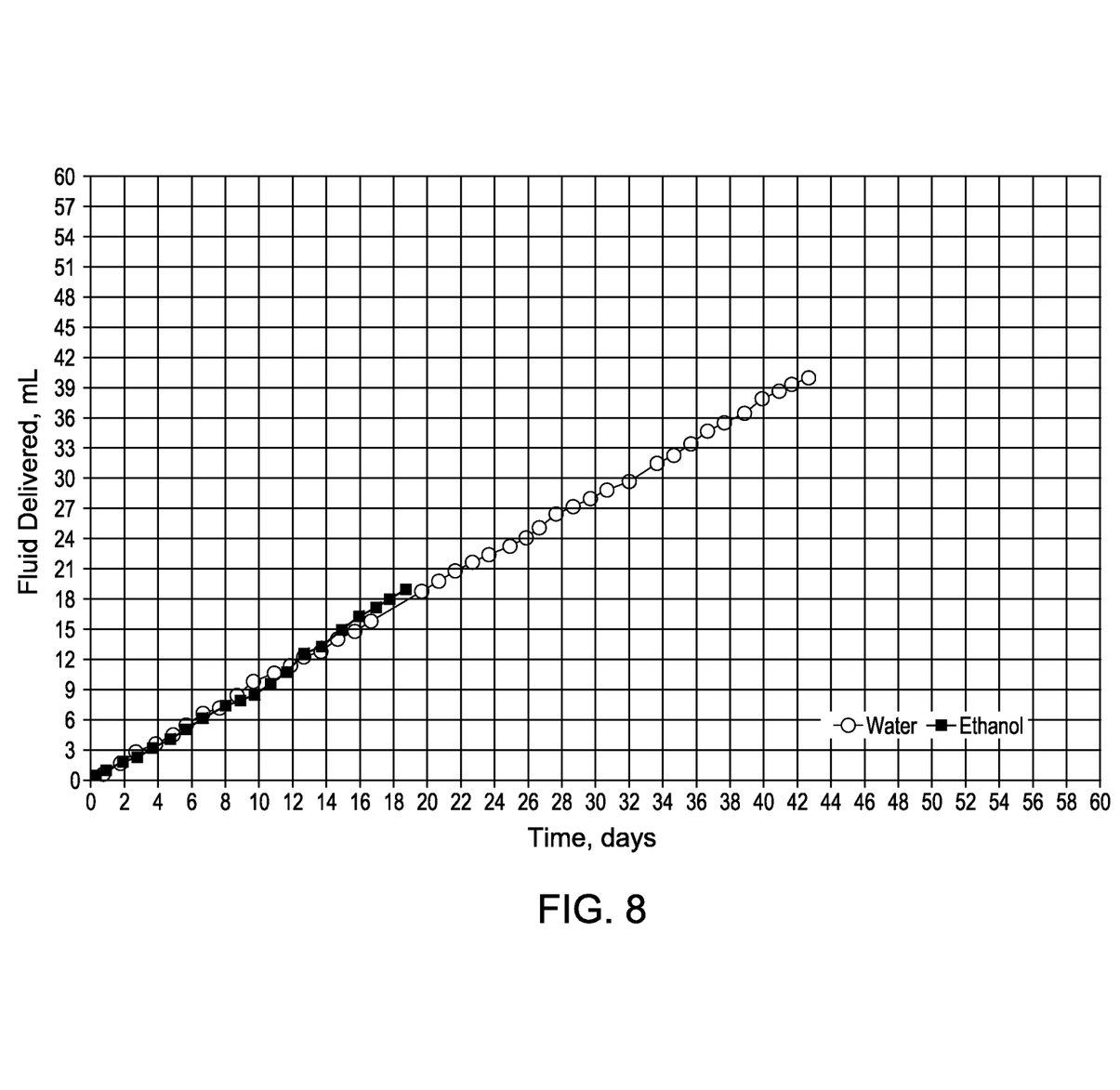
FIG. 8 is a graph depicting performance examples of the dispenser of the present invention.

FIG. 8 is a graph depicting performance examples of the dispenser of the present invention. The delivery of two fluids (namely water and ethanol) from two different dispensers is illustrated by the two depicted curves. In both instances the syringe barrel has a nominal 50 mL volume, and is constructed from polyethylene. The driver head assembly is configured for a single current of 200 microamps. This current corresponds to a theoretical gas (oxygen) generation rate of 1.10 cc/day. The fluid receiver for water is a Porex 5542 porous high density polyethylene cup that is 1.3 cm in diameter, and 2.4 cm long, and having an average pore size of 30-70 microns.

The fluid receiver for ethanol is a Dragon Shing Rotocasting Co. high molecular weight polyethylene cup 4 with a diameter of 1.3 cm and a length of 1.76 cm and an average pore size of 40 microns.

Since no fluid accumulation takes place in the receiver, the average fluid pumping rate and evaporation rate for both water and ethanol are identical and about 0.94±0.04 mL/day.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A method for continuously dispensing fluid at a low volumetric flowrate comprising the steps of:

first dispensing a fluid through a small orifice, said first dispensing being executed by a device comprising:
   an upright barrel defined by:
      a top end having a large opening; and
      a bottom end having said small orifice; and an internal chamber in fluid communication with said orifice and said large opening, said top end large opening juxtaposed over said small orifice such that said small orifice is located beneath said upright barrel and juxtaposed thereby;
   a drive head assembly sealing said large opening atop and juxtaposed over said upright barrel, said drive head assembly comprising:
      a head flange attached to seal said large opening atop said upright barrel, said head flange formed with a well formed therein, said well having an inflation orifice formed therethrough; and
      a driver base defining a boss configured to insert into said well and defined by an orifice formed therein;
   a bladder contained in said internal chamber and hanging from a head flange boss formed on said drive head assembly; and
   whereby said drive head assembly is configured to generate gaseous material, allow said generated gaseous material to pass through said driver base boss orifice and said inflation orifice so as to then operably inflate said bladder with said generated gaseous material to drive fluid residing in said internal chamber out through said small orifice at said bottom end of said barrel;
   ceasing said operation of said drive head assembly and deflating said bladder;
   disposing of said bladder, barrel and orifice;
   installing a replacement said bladder, a replacement said barrel and a replacement said small orifice on a bottom defined by said drive head assembly, said replacement barrel containing dispensable fluid therein;
   second dispensing a fluid through said installed small orifice, said second dispensing being executed by said replacement barrel device in response to said drive head assembly operably generating gaseous material and inflating said replacement bladder with said generated gaseous material; and
   wherein said bladder and said replacement bladder are impermeable to said generated gaseous material.

2. The method of claim 1, further comprising an unsealing step between said disposing step and said installing step, said unsealing step comprising removing a seal from said small orifice.

3. The method of claim 2, further comprising a cup installation step after said unsealing step, said cup installation step comprising attaching a porous cup to said replacement barrel to cover said unsealed small orifice.

4. The method of claim 3, wherein said installing step comprises installing a replacement said barrel defined by a replacement said head flange bonded to said replacement barrel, said head flange designed to cooperate with said drive head assembly to detachably seal thereto during said installing step.

5. The method of claim 1, wherein said first dispensing and second dispensing steps are executed by said drive head assembly of said device, wherein said drive head assembly further comprises actuator means for activating and deactivating said dispensing by rotating said drive head assembly in relation to said barrel and said replacement barrel devices.

6. The method of claim 5, further comprising an unsealing step between said disposing step and said installing step, said unsealing step comprising removing a seal from said small orifice.

7. The method of claim 6, further comprising a cup installation step after said unsealing step, said cup installation step comprising attaching a porous cup to said replacement barrel to cover said unsealed small orifice.

8. The method of claim 7, wherein said installing step comprises installing a replacement said barrel defined by a replacement said head flange bonded to said replacement barrel, said head flange designed to cooperate with said drive head assembly to detachably seal thereto during said installing step.

* * * * *